United States Patent [19]

Sinor et al.

[11] Patent Number: 5,030,560
[45] Date of Patent: Jul. 9, 1991

[54] METHOD FOR DRYING MAMMALIAN CELLS FOR USE IN SOLID PHASE IMMUNOASSAYS AND ARTICLES INCORPORATING SAME

[75] Inventors: Lyle T. Sinor; Ralph A. Eatz, both of Roswell, Ga.

[73] Assignee: Immucor, Inc., Norcross, Ga.

[21] Appl. No.: 267,014

[22] Filed: Nov. 4, 1988

[51] Int. Cl.$^5$ ............... G01N 33/543; G01N 33/544; G01N 33/552

[52] U.S. Cl. ..................... 435/7.21; 424/11; 427/2; 435/7.24; 435/725; 435/174; 435/176; 435/177; 435/260; 435/961; 435/963; 436/518; 436/527; 436/528; 436/826

[58] Field of Search ............... 435/7, 174, 176, 177, 435/7.21, 7.24, 7.25, 961, 963, 260; 436/518–521, 527, 528, 826, 522; 427/2; 424/11

[56] References Cited

U.S. PATENT DOCUMENTS

| | | | |
|---|---|---|---|
| 4,596,723 | 6/1986 | Kaufman et al. | 427/336 |
| 4,608,246 | 8/1986 | Bayer et al. | 436/521 |
| 4,666,829 | 5/1987 | Glenner et al. | 435/7 |
| 4,891,319 | 1/1990 | Roser | 435/176 |

FOREIGN PATENT DOCUMENTS

| | | |
|---|---|---|
| 0140489 | 1/1985 | European Pat. Off. |
| 0243818 | 5/1987 | European Pat. Off. |
| 0266077 | 11/1988 | European Pat. Off. |
| 8705300 | 9/1987 | World Int. Prop. O. |

Primary Examiner—David A. Saunders
Attorney, Agent, or Firm—Kokjer, Kircher, Bradley, Wharton, Bowman & Johnson

[57] ABSTRACT

A method for drying mammalian cells, such as erythrocytes, lymphocytes, leukocytes and platelets onto a solid-phase support for use in solid-phase immunoassays through use of a drying solution and an article for use in immunoassays prepared by such method. The method comprises immobilizing a monolayer of cells onto the solid-phase support by non-covalent binding. This is accomplished by staining the solid-phase support with an organic dye having a net positive charge which permits non-covalent binding of the cells which carry a net negative charge to the solid-phase support. These cells are dried or fixed to the solid-phase support by addition of a drying solution which comprises an aqueous solution of a monosaccharide, disaccharide, trisaccharide or cyclitol and a salt. The preferred monosaccharide is D-(31 )glucose and the preferred salt is sodium chloride. The preferred drying solution comprises a 1.0M solution of dextrose and a 154 mM solution of sodium chloride. The drying solution is contacted with the immobilized cells and immediately decanted and any excess water or drying solution is removed by drying the solid-phase support in a sealed pouch with a desiccant material for 3–8 days at between 2°–8° C. The preferred amount of time required for complete drying is 7 days at 2°–8° C.

16 Claims, No Drawings

METHOD FOR DRYING MAMMALIAN CELLS FOR USE IN SOLID PHASE IMMUNOASSAYS AND ARTICLES INCORPORATING SAME

BACKGROUND OF THE INVENTION

This invention relates in general to solid-phase immunoassays and, more particularly, to a method for drying mammalian cells adsorbed to a solid-phase support for use in solid-phase immunoassays and articles incorporating same.

Solid-phase immunological assay procedures have been developed to provide sensitive and specific immunological assays that are more convenient and easier for lab technicians to perform. In a solid-phase immunoassay, one component of the immunological reaction, either antigen or antibody, is immobilized onto the surface of a solid-phase support. The antigen or antibody may be immobilized directly onto the solid-phase support by a variety of methods known to those skilled in the art. In addition to antigens or antibodies, whole cells such as erythrocytes, leukocytes, lymphocytes, platelets or other mammalian cells can be immobilized to the surface of a solid-phase support for immunological assays specific for such cells. Each of these types of cells present antigens on its cell surface which can be used to detect antibodies in a biological fluid sample to be assayed. Also, specific antigens or antibodies can be adsorbed to the surface of the cells for other types of immunological assays. Thus, immunoassays involving cells of the type described above have been developed to determine the presence of antigens or antibodies in assays for blood groups and infectious disease agents, especially those directly affecting the cellular components of blood.

When whole cells are utilized in solid-phase immunoassays, present techniques used to fix these cells to the solid-phase support employ chemical agents which crosslink functional groups on the surface of the cells to functional groups on the surface of the solid-phase support. Typical chemical agents used for this purpose are glutaraldehyde and dimethyl suberimidate. The primary problem associated with the use of these agents for immunoassays involving whole mammalian cells is that while they fix the cells to the support, they also block some reactive groups which are responsible for antigenic activity. Due to the enormous complexity and multitude of antigenic determinants found upon the surface of cells, no single chemical crosslinking agent has been found which does not affect the antigenicity of the cell membrane. In those assays where only a single or only a few antigenic determinants must be maintained, chemical cross-linking agents can be utilized effectively. If all of the antigenic determinants must be maintained, however, as in the case of assays utilizing red cell monolayers used to detect irregular antibodies in patient sera, chemical cross-linking agents cannot be used since they block some of the potential reactive groups.

Whole mammalian cells may also be fixed by agents which draw water out of the cell. Typical agents that draw water out of or replace water within cells are methanol, acetone and dimethyl sulfoxide. Methanol and acetone have been used to fix tissue slices for microscopic examination, but are not applicable for use with immobilized monolayers of cells such as erythrocytes, lymphocytes, or platelets because they tend to destroy antigens on the surface of the cells, especially red blood cells. Additional problems with chemicals like methanol and acetone are the problems associated with hazardous waste disposal requirements, their flammability and noxiousness if vapors escape into the laboratory. Agents such as dimethyl sulfoxide, sugars, and amino acids which replace water in the cell, have also been used to preserve suspended cells, but these cells must be stored frozen and washed prior to use.

Whenever cells are stored frozen, there is the subsequent problem of breaking the cell membrane during freeze-thaw cycles and thus a consequent loss of cells. Additional problems associated with methods that involve freezing of the cells is the cost of maintaining freezers and the loss of laboratory space and the inconvenience of having to thaw and wash the cells prior to use.

Thus, there is a need in the field of immunology for a method for drying or fixing monolayers of mammalian cells to solid-phase supports for use in immunoassays which obviate the problems discussed above.

It is therefore a primary object of the present invention to provide a method for drying monolayers of mammalian cells adsorbed onto a solid-phase support for use in immunoassays in a manner maintaining the complete antigenicity of the cell surface antigens and in a manner permitting the solid-phase supports having these dried cell monolayers thereon to be stored at ambient temperatures thereby avoiding the problems of storage at sub-freezing temperatures.

It is another object of the present invention to provide articles for use in solid-phase immunoassays where the mammalian cells dried thereon can be stored at room temperature for at least six months and remain capable of performing sensitive and accurate immunoassays.

It is a further object of the present invention to provide a method for drying monolayers of mammalian cells adsorbed onto a solid-phase support for use in immunoassays that reduces the costs involved in such assays by extending the shelf-life of the cell monolayer.

It is still another object of the present invention to provide a method for drying monolayers of mammalian cells adsorbed onto a solid-phase support for use in immunoassays where the drying solution is not harmful to the monolayer nor interferes with performance of the assay.

It is an aim of the present invention to provide a method for drying monolayers of mammalian cells such as erythrocytes, lymphocytes, leukocytes and platelets onto a solid-phase support for use in immunoassays where the drying solution comprises an aqueous solution of a monosaccharide disaccharide, trisaccharide or cyclitol and a salt.

Other and further objects will become apparent from the following description and claims.

SUMMARY OF THE INVENTION

We have discovered that a monosaccharide, disaccharide, trisaccharide or cyclitol containing salt solution of the appropriate hypotonicity can be used to preserve monolayers of erythrocytes, leukocytes, lymphocytes and platelets immobilized onto solid-phase supports while still maintaining the complete antigenic activity of the cells. Monolayers of immobilized cells that have been subjected to the procedure of the present invention are capable of being stored at room temperature for at least six months without any significant loss in accuracy or sensitivity. The preferred method of immobilizing the subject cells to the solid-phase support is by adsorption of the cells to a solid-phase support previously stained with an organic dye having a net positive charge. To this monolayer of immobilized cells, the drying solution is added.

The preferred concentration range of the monosaccharide, disaccharide, trisaccharide or cyclitol in the drying solution is between 0.1 moles/liter-3.0 moles/liter. The preferred range of the salt in the drying solution is from 50 millimoles/liter-377 millimoles/liter. The preferred salt to be used is sodium chloride, but other salts such as potassium chloride and sodium phosphate may be utilized with equal effectiveness and applicability. While any monosaccharide, disaccharide, trisaccharide, or cyclitol may be utilized, the preferred substance is dextrose or D(-)glucose and the preferred drying solution comprises 1.0 moles/liter dextrose and 154 millimoles/liter NaCl.

DESCRIPTION OF THE PREFERRED EMBODIMENT

Solid-phase immunoassays utilize a wide array of articles as the solid support structure. The support often takes the form of test tubes, beads, sheets of material, petri dishes, membranes or Microtitre ® plates. Other types of supports or forms of supports are useful in carrying out the aims and objects of the present invention and are equally applicable.

The solid-phase can be composed of an organic polymer such as polystyrene, polypropylene, polyvinylchloride or nylon. In addition, materials that are capable of binding a monolayer of mammalian cells or capable of being adapted to bind a monolayer of mammalian cells are equally applicable, such as glass.

The most preferred solid-phase support for carrying out immunoassays embodying the present invention are Microtitre ® plates having a plurality of recessed wells. The Microtitre ® plates are preferably made of an organic polymer, and most preferably polystyrene.

In keeping with the aims and objects of this invention, it is desirable that the monolayer of cells be adsorbed to the solid-phase support surface in a manner that leaves intact the complete antigenicity of the mammalian cell being utilized. This is best accomplished by the absorption of an organic dye, or dyes, onto the surface of an organic polymer surface. For the purpose of immobilizing human erythrocytes, lymphocytes, leukocytes or platelets, each of which carry a net-negative surface charge, the dye must possess a net positive charge. When the cells come into physical contact with the dye, the cells become immobilized by adsorption to the dye by non-covalent interactions, such as ionic bonding, hydrogen bonding, Van der Waal's forces, and hydrophobic bonding. In this manner, a monolayer of immobilized cells results following the washing away of unbound cells. The cell monolayer may then be used in immunological assays, such as solid-phase red cell adherence, for the detection of antibodies to antigens found on the surface of the immobilized cells. Specific antibodies may also be adsorbed onto the cell monolayers in order to detect specific antigens in biological test solutions.

The dyes which have been found to be most useful to adsorb mammalian cells are organic dyes possessing a net positive charge and that have a hydrophobic aromatic ring structure. Any dye that has such a net positive charge and a hydrophobic aromatic ring structure that adheres to a solid-phase support has been found to be capable of immobilizing mammalian cells, such as erythrocytes, lymphocytes, leukocytes and platelets. The particular dyes that are applicable and a method for adsorbing such dye to the solid-phase support are discussed in our co-pending patent application entitled "AN ARTICLE FOR PERFORMING IMMUNOLOGICAL ASSAYS UTILIZING ORGANIC DYES AND METHODS FOR PRODUCING AND UTILIZING SAME", filed on July 5, 1988, Ser. No. 215,041, now U.S. Pat. No. 4,963,478, which is hereby incorporated by reference.

In general, the most preferred dyes for this purpose have been found to be Alcian blue and Alcian yellow. Alcian blue is a phthalocyanin and Alcian yellow is an azo dye, each possessing a net positive charge. Other dyes which possess a net positive charge that may also be used include diazo dyes, polyazo dyes, diazonium and tetrazonium salts, tetrazolium salts, triphenylmethanes, xanthenes or acridines, quinoline dyes, thiazoles, indamines, azins, aminoazins, saffronins, thiazins, and phthalocyanins.

If Alcian blue is to be used, it is first dissolved in isotonic saline at a concentration between 1 ug/ml to 1 g/ml. The preferred concentration is 0.1 mg/ml and between 50-250 ul is applied to the organic polymer support so as to completely cover the solid-phase support. The dye is left in contact with the solid-phase support for a sufficient period of time and then excess dye is washed away. For most dyes, the contact time need only be an immediate contact, but for some other dyes an extended period of time is necessary to achieve absorption of the dye to the solid-phase support. If Alcian yellow is to be used, it must first be dissolved in a sufficient quantity of 100% methanol since Alcian yellow is not soluble in aqueous solutions. An equal volume of isotonic saline is then added to the dissolved Alcian yellow to a final concentration range of between 1 ug/ml to 1 g/ml, and most preferably 0.1 mg/ml. Again, between 50-250 ul of the Alcian yellow solution is applied to the solid-phase support, preferably a Microtitre ® plate, to achieve absorption of the dye onto the solid-phase support.

To create the monolayers of cells onto the solid-phase support stained with the organic dye carrying a net positive charge, the cells to be immobilized must first be washed free of contaminating proteins. Suitable wash solutions for red blood cells are isotonic saline, reagent red blood cell diluent (from Immucor, Inc.), or phosphate buffered saline, pH 7.4. For platelets, an Alsever's solution or a modified Alsever's solution, or platelet wash and storage solution (from Immucor, Inc.) can be used.

The cells utilized in this invention are obtained from standard sources known in the industry. After the cells are washed, they are typically suspended in isotonic saline. The concentration of the cells in suspension for the purposes of this invention ranges between 0.1% to 0.4% (V/V). The most useful range is between 0.1%-0.2% (V/V).

The washed cell suspension is added to the dye coated solid-phase support, and the cells are permitted to come into contact with the dye by settling of the cells or by centrifugation. After allowing an appropriate period of time for the cells to bind with the organic dye, excess cell solution is decanted leaving a monolayer of cells immobilized to the dye coated solid-phase support. One to five minutes is typically necessary if the centrifugation method is used and 40-60 minutes if the cells are allowed to settle by gravity, When smaller cells, such as platelets, are used, it is best to allow them to settle overnight to ensure a complete contact and formation of a uniform monolayer of cells.

Once the monolayer of cells has been adsorbed to the solid-phase support, the drying solution of the present invention is utilized to dry or fix the cells to the solid-phase support. It has been found that when red blood cells are utilized as the monolayer of cells, better results, in the context of a more sensitive assay, are achieved by lysing the cells comprising the monolayer with an appropriate lyse solution prior to addition of the drying solution. For platelets, lymphocytes and leukocytes, the lysing step is not necessary.

Generally, the drying solution comprises an aqueous solution containing a salt and a sugar selected from the group consisting of monosaccharides, disaccharides, trisaccharides and cyclitols. The monosaccharide, disaccharide, trisaccharide or cyclitol useful in the present invention can be selected from the group consisting of D-(+)Raffinose, L-(−)sorbose, D-(+)Trehalose, D-(+)xylose, D-(−)glucose, D-(−)sorbitol, sucrose, L-(+)Arabinose, D-(−)cellobiose, D-(−)fructose, D-(+)Galactose, myo-inositol (a cyclitol), α-lactose, D-(+)lyxose, maltose and D-(+)mannose. More particularly, the most useful substances from this group are D-(−)glucose, sucrose, D-(−)sorbitol, D-(+)lyxose, myo-inositol, D-(+)cellobiose and L-(−)sorbose. The most preferred sugar from the groups above is dextrose or D-(−)glucose (from Fisher) which has the chemical formula $C_6H_{12}O_6 \cdot H_2O$. It is also to be conceived that the corresponding enantiomeric sugars of those listed above can also be utilized. The drying solution is prepared having a monosaccharide, disaccharide, trisaccharide or cyclitol concentration of between 0.1 moles/liter-3.0 moles/liter. The most preferred concentration is 1.0 M dextrose which works best with erythrocytes and platelet cell monolayers.

The salts useful in the present invention include those from the group consisting of sodium chloride (NaCl), potassium chloride (KCl), and sodium phosphate. The preferred concentration range of the salt in the drying solution is between 50 millimoles/liter-377 millimoles/liter. The preferred salt is sodium chloride present in the drying solution at a concentration of 154 mM.

The drying solution is prepared with distilled and/or de-ionized water in clean glassware to avoid any contaminating proteins being introduced into the assay system.

Once the drying solution is prepared, it is then added to the surface of the solid-phase support containing the cell monolayer, such as a test tube or more preferably, a Microtitre ® plate having recessed wells. The volume of drying solution necessary to be added to cover a well of a Microtitre ® plate should be enough to entirely cover the cell monolayer. Twenty five ul-150 ul is a sufficient quantity with 100 ul being the preferred amount. The optimum period of time that the drying solution needs to be incubated on the cell monolayer and the optimum incubation temperature must be determined for each different type of cell monolayer tested. One procedure which can be utilized to determine the optimum period of time and the optimum incubation temperature is to prepare a plurality of wells with a single source of cells and to add the same amount of drying solution to each well and allow the wells to be removed for assays at intervals of time ranging from an immediate contact and decanting to up to 4 hours incubation. If all other parameters are maintained constant, an evaluation of the results of the assays will give the optimum incubation time necessary to obtain optimum results. A similar test may be run with only the temperature being varied. The optimum incubation time and temperature for addition of the drying solution to monolayers of human platelets, leukocytes, lymphocytes and erythrocytes is an immediate addition and decanting of the drying solution at room temperature. The drying solution is best removed from the cell monolayers by flicking over a sink or by vacuum aspiration. Other methods of removing the drying solution are equally applicable.

The test tube or Microtitration plate is then placed in a foil pouch or packet with a dessicant material therein and sealed. The pouch should have very little or no water permeability and all water in the test tube or Microtitration plate must be absorbed by the dessicant material. The preferred dessicant material for this purpose is molecular sieve dessicants obtained from sources known in the industry. Other dessicant materials such a diatomacious earth and silica particles or vacuum drying can be substituted, but with less satisfactory results. The amount of dessicant material necessary is an amount having a capacity to absorb an amount of water greater than that which exists on the solid phase support. It has been found that if 2 gram capacity molecular sieve dessicants are used, addition of 2-3 of such packets is sufficient. The acceptable range of temperature and time needed for absorption of the water on the solid-phase support by the dessicant in a sealed pouch has been found to be 3-8 days at between 2°-8° C. with the most useful range being 5-7 days at between 2°-8° C. For human erythrocytes, lymphocytes, leukocytes and platelets, optimum drying time is 7 days at between 2°-8° C. After this absorption period has passed, the sealed solid phase support may be stored at room temperature or at lower temperatures for at least up to six months without any loss in assay accuracy or efficiency.

Although not absolutely necessary, it is preferable to lyse red blood cell monolayers prior to addition of the drying solution to empty the cell of some of its intracellular contents. This aids in the drying procedure by permitting the drying solution better access to the inside of the cell. The lyse solution can be chosen from a solution of de-ionized water to a 120 mM NaCl salt solution. Hypertonic solutions of between 300-800 mM NaCl may also be used. The most preferred lysing solution is 80 mM NaCl.

After the red blood cell solution has been allowed to contact with the stained solid-phase support, excess cell solution is decanted and the lyse solution is added directly to the cell monolayer and allowed to incubate for between 1 and 30 minutes. The optimum incubation time has been found to be 1 minute for erythrocytes. The lyse solution is decanted and the article is washed twice with isotonic saline. The drying solution is then added as described above.

Salt solutions other than NaCl may also be used for the lyse solution such as phosphate buffered saline (PBS), potassium chloride, Tris(hydroxymethyl)aminomethane (TRIS) and tissue culture media.

To use the solid-phase support having a monolayer of the dried mammalian cells thereon, the pouch is opened and the biological fluid to be tested is added to the test tube or Microtitre ® plate well. Typically, the biological fluid is human serum or plasma. A low ionic strength additive, such as a glycine solution at approximately 19 g/L, may be added to the wells at this time also. The glycine solution may additionally contain a preservative such as thimerosol and a dye. Following a suitable incubation period, the test tube or Microtitre ® plate wells are washed to remove unbound plasma or serum components. The presence of antibodies binding specifically to the immobilized cell monolayer may be detected by any number of methods known to the art, such as radioimmunoassays, enzyme linked immunosorbent assays (ELISA), immunofluorescence or solid-phase red cell adherence.

Solid-phase supports prepared according to the present invention have utility in a wide variety of immunological assays including antibody screening for the detection of unexpected antibodies directed toward human erythrocytes or human platelets, antibody screening to determine the identity of an antibody in a biological sample by using a panel of erythrocytes or platelets having varying, known antigen patterns, reverse ABO grouping, forward ABO grouping and D-typing, erythrocyte phenotyping and the detection of antibodies directed toward mammalian tissue cells.

The following examples are given by way of illustration only and have no limiting character.

EXAMPLE 1

To perform an immunoassay for the detection of unexpected antibodies directed toward human erythrocytes utilizing the teachings of the present invention, a Microtitre ® plate having a plurality of recessed wells is first treated with a sufficient quantity of Alcian yellow at a concentration of 0.1 mg/ml so that all of the wells are covered by the Alcian yellow solution. The Alcian yellow solution is allowed to remain in contact with the Microtitre ® plate for about thirty minutes and excess dye solution is removed. A monolayer of human erythrocytes or red blood cells is formed on the stained plate by addition of 100 microliters of a 0.2% (V/V) suspension of human RBC's in saline or reagent red blood cell diluent per well. The erythrocytes are allowed to settle by gravity for one hour at room temperature. The cells are then lysed by the addition of 100 microliters per well of 80 mm NaCl. The lysing solution is allowed to incubate for one minute at room temperature in the wells and is then removed by aspiration. The plate is washed at least two times with isotonic saline to remove unbound erythrocytes by an automatic washing apparatus or by manual methods. One hundred microliters of the drying solution containing 1.0 M dextrose and 154 mM sodium chloride is added to each well. Immediately following addition of the drying solution, each well is aspirated to remove any excess drying solution. The Microtitre ® plate is then placed in an inverted position into a foil packet or pouch having at least two, 2 g capacity molecular sieve dessicant packets therein. The pouch is sealed with heat and dried for seven days at 2°-8° C.

In order to use the Microtitre ® plate in an immunological assay, the foil package is opened and one drop of a biological fluid such as serum or plasma or a control is added to each well. Two drops of a 19 g/L solution of glycine with a preservative and a dye for color is also added to each well. These solutions are allowed to incubate in the wells at 37° C. for 15 minutes. After the incubation period, the wells of the Microtitre ® plate are washed three times with saline, preferably by an automatic washing apparatus such as the Bio-Tek model EL-402. One drop of anti-IgG coated indicator red blood cells is then added to each well. The Microtitre ® plate is centrifuged at 450×G for one minute. The plate is then examined for adherence or lack of adherence of the indicator red blood cells to the erythrocyte cell monolayer. A positive reaction is seen by adherence of the indicator red cells over the reaction surface. A negative reaction forms a discreet button of indicator red cells at the bottom of the wells showing no adherence.

Thus, if the biological fluid being tested has antibodies directed toward the erythrocyte cell monolayer, it binds to the erythrocyte monolayer. The anti-IgG coated indicator red blood cells correspondingly bind to the antibody thus bound when they are added to the wells. This gives the positive reaction described. If no antibodies directed toward the erythrocytes are present in the biological fluid being tested, the anti-IgG coated indicator red blood cells would have no complementary immunological component to bind to and would collect at the bottom of the well as a discreet button as described above. Immunological assays utilizing the above method and solid-phase support consistently yield results more sensitive than those obtained by standard tube-tests.

EXAMPLE 2

The present invention can be utilized to prepare a Microtitre ® plate having an antibody panel for assays for the detection of unexpected antibodies directed toward human erythrocytes. A Microtitre ® plate is prepared essentially as in Example 1, except that a panel of human erythrocytes with known and varying blood group antigen phenotypes or patterns is adsorbed to individual wells of the stained Microtitre ® plate. The erythrocytes are lysed, washed and dried as described in Example 1. In order to detect unexpected antibodies and to determine the specific antibody detected in a test serum or plasma sample, one drop of such serum or plasma is added to each panel well of dried erythrocytes on the Microtitre ® plate. The assay is performed as described in Example 1 and the specificity of the antibody in the sample causing positive reactions in individual wells can then be determined by interpretation of the panel member phenotypes of the individual wells showing the positive reaction.

EXAMPLE 3

The present invention can be utilized to prepare Microtitre ® plates useful as an antibody screen for the detection of unexpected antibodies directed toward human platelets. A Microtitre ® plate is stained with Alcian yellow as described in Example 1. A platelet cell monolayer is formed by addition of 100 microliters of a 0.1% (V/V) suspension of platelets and modified Alsever's solution (from Immucor) to each of the Microtitre ® plate wells. The platelets are allowed to settle by gravity for 24 hours at 2°-8° C. Excess platelet solution is decanted and the plate is washed twice with an isotonic saline solution. One hundred microliters of a drying solution comprising 1.0 M dextrose and 154 mM NaCl is added to each well and immediately decanted. The plate is placed in a foil pack with molecular sieve dessicant and allowed to dry for 7 days at 2°-8° C. In order to test for unexpected antibodies in human biological fluid, one drop of serum, plasma or control is added to each well and allowed to incubate in the wells at 37°

C. for 15 minutes. The wells are washed three times with an isotonic saline solution and one drop of indicator red-blood cells is added to each well. The plate is centrifuged at 900×G for one minute and then examined for adherence or lack of adherence of the indicator red blood cells to the platelet monolayer. A positive reaction shows adherence of the indicator red blood cells over the well surface. A negative reaction forms a discreet button of indicator red blood cells at the bottom of the wells.

Thus, if the biological fluid being assayed has antibodies directed toward platelets, it binds to the platelet monolayer. If no such antibodies are present in the biological fluid, the indicator cells collect at the bottom of the well. Assays utilizing the above method and solid-phase support consistently yield results more sensitive than those obtained by standard tube-tests.

EXAMPLE 4

A Microtitre ® plate prepared in accordance with the present invention may be used to prepare an antibody panel for the detection of unexpected antibodies directed toward human platelets. This assay is prepared and performed the same as the immunoassay described in Example 3 except that a panel of human platelets with known and varying antigen phenotypes or patterns is prepared in individual wells of the Microtitre ® plate. The Microtitre ® plate is washed and dried by addition of the drying solution in a manner corresponding to that described in Example 3. The Microtitre ® plate is utilized in the immunoassay by addition of one drop of serum or plasma to each individual well of dried platelets. The assay is performed as described in Example 3. The specificity of the antibody in the sample in individual wells causing positive reactions can then be determined by interpretation of the individual panel member phenotypes.

EXAMPLE 5

The assay of Example 4 may be utilized to permit the identification of specific platelet antibodies other than HLA by chloroquine removal of the HLA antigen prior to addition of the drying solution. The procedure as set out in Example 4 is modified as follows: Once the platelet monolayers have been prepared, 100 microliters/well of 100 mg/ml chloroquine in 20 mM MES buffer, pH 6.0 is added. Control wells contain only 20 mM MES buffer. The Microtitre ® plate is incubated at 37° C. for one hour and washed four times with saline. The drying solution as described in Example 4 is added and the final preparation of the Microtitre ® plate and the assay proceeds as described in Example 4.

EXAMPLE 6

The present invention can be utilized to prepare solid-phase supports suitable for performing reverse ABO grouping assays. A Microtitre ® plate is stained with Alcian yellow as described in Example 1 and 100 microliters of a 0.2% (V/V) suspension of $A_1$ and a similar suspension of B red blood cells in saline or reagent red blood cell diluent are added to a plurality of separate wells. The red blood cells are allowed to settle by gravity for 40-60 minutes at room temperature. One hundred microliters of 80 mM sodium chloride is added to each well to lyse the red blood cells. The lysing solution is allowed to incubate for one minute at room temperature in the wells and is then removed by aspiration. The Microtitre ® plate is then washed two times with an automatic washing apparatus with isotonic saline. One hundred microliters of a drying solution comprising 1.0 moles/liter dextrose and 154 millimoles/liter sodium chloride is added to each well. The drying solution is removed by aspiration immediately after its addition to the wells and the Microtitre ® plate is placed in an inverted position into a foil pouch having molecular sieve dessicant therein. The pouch is sealed with heat and allowed to dry at 2°-8° C. for five days.

In order to perform the reverse ABO grouping assays, the foil package is opened and one drop of serum, plasma or a control is added to each well and allowed to incubate for 15 minutes at 37° C. The Microtitre ® plate is washed three times with an automatic washing apparatus using saline. One drop of $A_1B$ indicator red blood cells is added to each well. The Microtitre ® plate is centrifuged at 450×G for one minute and the plate is examined for adherence or lack of adherence of the indicator red blood cells to the erythrocyte cell monolayer. If the patient's biological fluid sample has antibodies to $A_1$ type red blood cells, they will bind to wells having $A_1$ type red blood cell monolayers and a positive reaction is seen by adherence of the indicator cells over the reaction surface. In similar fashion, if the patient's serum or plasma has antibodies to B type red blood cells, they will bind to wells having B type red blood cell monolayers. A negative reaction forms a discreet button of indicator red blood cells at the bottom of the well showing no adherence.

EXAMPLE 7

The present invention may be utilized to prepare solid phase supports useful in performing assays to determine forward ABO grouping and D typing. A Microtitre ® plate stained with Alcian yellow is prepared as described in Example 1 and 100 microliters of separate 0.2% (V/V) suspensions of $A_1$, B, and 0-Rh positive red blood cells in saline is added to separate wells. The red blood cells are allowed to settle by gravity for one hour at room temperature. After the cells have settled, excess cell solution is decanted from the plate. The cell monolayers are then sensitized by addition of 100 microliters of the appropriate dilution of anti-A, anti-B and anti-D into the appropriate wells. The antisera is incubated for 60 minutes at 37° C. in the well and excess antisera removed by aspiration. One hundred microliters of 80 mM sodium chloride as a lysing solution is then added to each well and allowed to incubate for one minute at room temperature. The excess lysing solution is removed by aspiration and the plate is washed twice with isotonic saline. A drying solution comprising 100 microliters of 1.0 moles/liter dextrose and 154 millimoles/liter sodium chloride with 0.5% bromelain is added to each well. The drying solution is removed by aspiration immediately after its addition to the well and the Microtitre ® plate is placed in an inverted position into a foil packet with molecular sieve dessicants. The foil packet is sealed with heat and allowed to dry at 2°-8° C. for seven days.

To perform forward ABO grouping and D typing assays utilizing the Microtitre ® plate prepared as above, one drop of a 0.2-0.3% (V/V) suspension of test red blood cells diluted in saline is added to each well and allowed to incubate at 37° C. for 15 minutes. The Microtitre ® plate is then centrifuged at 450×G for one minute. The plate is examined for adherence or lack of adherence of the test red blood cells to the sensitized erythrocyte monolayer. A positive reaction is seen by adherence of the cells over the reaction surface. If the test red blood cells adhere to the wells containing $A_1$ red blood cells with anti-A antisera, the test red blood cells are A-type cells. If the test cells are B type, they will bind to wells having anti-B adsorbed to the cells. AB type red blood cells will bind to both anti-A and anti-B sensitized cells and 0-type blood cells will not adhere to any of the cells. Test red blood cells that are D+ bind to the wells carrying anti-D, but cells that are D− will not. A negative reaction forms a discreet button of red cells at the bottom of the well showing no adherence.

EXAMPLE 8

The present invention is utilized in preparing solid-phase supports useful in assays to determine red blood cell phenotyping. Microtitre ® plates are again stained with Alcian yellow as described in Example 1 and monolayers of cells are prepared in individual wells by addition of 100 microliters of a 1% (V/V) suspension of individual solutions of red blood cells in saline with known antigen blood group phenotypes. The cell suspensions are allowed to settle by gravity for one hour at room temperature and excess solution is removed by decanting. The cell monolayers are then sensitized with 100 microliters of the appropriate dilution of an antisera of interest and incubated for 60 minutes at 37° C. The antisera of interest will be the antibody specific for a particular known antigen on the cells forming the monolayer. The cell monolayer is then lysed by addition of 100 microliters/well of 80 millimolar sodium chloride with the excess lysing solution removed by aspiration after one minute incubation at room temperature. The plate is then washed twice with isotonic saline by the appropriate method. One hundred microliters of a drying solution is then added to each well with the drying solution comprising 1.0 moles/liter dextrose and 154 millimoles/liter sodium chloride. The drying solution is removed by aspiration immediately and the Microtitre ® plate is placed into a foil packet in an inverted position with molecular sieve dessicant. The packet is sealed with heat and allowed to dry at 4° C. for seven days.

To perform the red blood cell phenotyping assays, the Microtitre ® plate is removed from the foil package and one drop of a 0.2–0.3% (V/V) suspension of test red blood cells previously diluted in saline is added to each well and allowed to incubate at 37° C. for 15 minutes. The Microtitre ® plate is centrifuged at 450×G for one minute and the plate is then examined for adherence or lack of adherence of the test red blood cells to the erythrocyte cell monolayer. A positive reaction is seen by adherence of the cells over the reaction surface and shows that the test red blood cells contain the antigen complementary to the antibody sensitized to the cell monolayer. A negative reaction forms a discreet button of red blood cells at the bottom of the well showing no adherence. In this manner, the phenotype of test red blood cells may be determined.

EXAMPLE 9

The present invention can be utilized to prepare a Microtitre ® plate for the detection of unexpected antibodies directed toward human erythrocytes by an enzyme-linked immunoabsorbent assay (ELISA). The microplate is prepared as in Example 1. In order to detect unexpected antibodies in a test serum or plasma sample, one drop of such serum or plasma is added to each well of dried erythrocytes, followed by 2 drops of a low ionic strength solution. These solutions are allowed to incubate in the wells at 37° C. for 45 minutes. After the incubation period the wells of the Microtitre ® plate are washed four times with saline, preferably by an automatic washing apparatus. To each well 100 ul of an alkaline phosphatase conjugated anti-human IgG solution is added. The enzyme conjugated anti-IgG solution is incubated for 1 hour at 37° C. The conjugated anti-human IgG will bind immunologically in those wells in which IgG from the test sample has bound to the dried red cell monolayer (positive test) and is not washed away in the following wash step. The conjugated anti-human IgG in a negative well (no IgG from the test sample has bound to the dried red cell monolayer) does not bind and is washed away in the following wash step. The wells of the microplate are washed four times with saline. One hundred uls of a solution of the enzyme substrate, comprised of 1.0 mg/ml p-nitrophenol phosphate (PNPP) in 10% diethanolamine-$dH_2O$ is added to the wells. Following a 30 minute incubation at room temperature, the absorbance of the wells at 405 nm is measured by a microplate spectrophotometer. The alkaline phosphatase enzyme conjugated to the anti-human IgG in a positive well enzymatically cleaves the PNPP substrate resulting in a yellowish-green color which is visible by eye or at 405 nm's by spectrophotometer. In a negative well (no alkaline phosphatase conjugated anti-IgG present) the PNPP substrate is not enzymatically degraded and appears visually clear.

From the foregoing, it will be seen that this invention is one well adapted to attain all the ends and objects hereinabove set forth.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative and not in a limiting sense.

Having thus described the invention, what is claimed is:

1. A method for drying mammalian cells on a solid-phase support for use in solid-phase immunoassays, said method comprising the steps of:
   immobilizing whole mammalian cells to said solid-phase support while leaving intact substantially complete antigenicity of said mammalian cells;
   lysing said immobilized cells;
   contacting said immobilized cells with an effective quantity of a drying solution comprising an aqueous mixture of (a) a salt and (b) a monosaccharide, disaccharide, trisaccharide or cyclitol,
   which mixture is capable of reaching the interior of said cells;
   removing said drying solution from contact with said immobilized cells whereby both the inside and outside of said cells are dried.

2. The method as set forth in claim 1 wherein said lysing is accomplished by addition of a lysing agent selected from the group consisting of de-ionized water and a salt solution to said immobilized cells.

3. A method as set forth in claim 2 wherein said lysing agent comprises a NaCl solution.

4. A method as set forth in claim 2 wherein said lysing agent comprises an 80 mM NaCl solution.

5. The method as set forth in claim 1 wherein said solid-phase support is made of an organic polymer or glass.

6. The method as set forth in claim 1 wherein said monosaccharide, disaccharide, trisaccharide or cyclitol is selected from the group consisting of D-(−)glucose, sucrose, D-(−) D-(+)lyxose, myo-inositol, D-(+)cellobiose and L-(−)sorbose.

7. The method as set forth in claim 6 wherein said monosaccharide is D-(−) glucose.

8. The method as set forth in claim 1 wherein said monosaccharide, disaccharide, trisaccharide or cyclitol in said mixture has a concentration of between 0.1 M–3.0 M.

9. The method as set forth in claim 1 wherein said salt in said mixture is present in a concentration of between 50 mM–377 mM.

10. The method as set forth in claim 1 wherein said salt is selected from the group consisting of sodium chloride, potassium chloride or sodium phosphate.

11. The method as set forth in claim 1 wherein said salt in said mixture is 154 mM sodium chloride.

12. The method as set forth in claim 1 wherein said drying solution is added to said solid phase support in a quantity to entirely cover said immobilized cells.

13. The method as set forth in claim 1 wherein said removal step further comprises the steps of:
    decanting said drying solution from said solid-phase support; and
    placing said solid-phase support in a sealed container with a dessicant material therein.

14. The method as set forth in claim 1 wherein said mammalian cells are selected from the group consisting of erythrocytes, platelets, leukocytes and lymphocytes.

15. The method as set forth in claim 1 wherein said mammalian cells are erythrocytes or platelets.

16. A method as set forth in claim 1 wherein said immobilizing comprises the steps of:
    coating said solid-phase support with an organic dye having a net positive charge and a hydrophobic aromatic ring structure; and
    contacting said cells with the coated solid-phase support.

* * * * *

UNITED STATES PATENT AND TRADEMARK OFFICE
CERTIFICATE OF CORRECTION

PATENT NO. : 5,030,560
DATED : July 9, 1991
INVENTOR(S) : Lyle T. Sinor et al.

It is certified that error appears in the above-identified patent and that said Letters Patent is hereby corrected as shown below:

Column 3, lines 45-46, "absorp-tion" should read -adsorption-
Column 4, line 33, "absorption" should read -adsorption-
Column 4, line 42, "absorption" should read -adsorption-
Column 6, line 19, "absorbed" should read -adsorbed-
Column 6, line 26, "absorb" should read -adsorb-
Column 6, line 31, "absorption" should read -adsorption-
Column 6, line 37, "absorption" should read -adsorption-
Column 11, line 65, "immunoabsorbent" should read -immunosorbent- Signed and Sealed this Twenty-eighth Day of November, 2000

Attest:

Q. TODD DICKINSON

*Attesting Officer*   *Director of Patents and Trademarks*